United States Patent
Hui et al.

(10) Patent No.: US 10,190,083 B2
(45) Date of Patent: Jan. 29, 2019

(54) METHOD AND DEVICE FOR PATTERNING AN INTERFACE

(71) Applicant: THE REGENTS OF THE UNIVERSITY OF CALIFORNIA, Oakland, CA (US)

(72) Inventors: Elliot En-Yu Hui, South Pasadena, CA (US); Jiang Li, Irvine, CA (US); Monica Young Kim, Fullerton, CA (US); Allison Lee Curtis, Irvine, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 219 days.

(21) Appl. No.: 15/140,118

(22) Filed: Apr. 27, 2016

(65) Prior Publication Data
US 2016/0310989 A1    Oct. 27, 2016

Related U.S. Application Data

(60) Provisional application No. 62/153,420, filed on Apr. 27, 2015.

(51) Int. Cl.
*B05D 1/32* (2006.01)
*C12M 1/32* (2006.01)
(Continued)

(52) U.S. Cl.
CPC ............ *C12M 23/12* (2013.01); *C12M 23/20* (2013.01); *C12M 33/00* (2013.01); *C12M 35/08* (2013.01); *C12N 1/00* (2013.01)

(58) Field of Classification Search
None
See application file for complete search history.

(56) References Cited

U.S. PATENT DOCUMENTS

2002/0182633 A1    12/2002    Chen et al.
2004/0214313 A1    10/2004    Zhang et al.
(Continued)

FOREIGN PATENT DOCUMENTS

WO    WO2008109883 A2    9/2008
WO    WO2010036913 A3    7/2010

OTHER PUBLICATIONS

Ibidi Website, "Culture-Insert 4 Well in μ-Dish 35mm, high" (2016).*

(Continued)

*Primary Examiner* — Nathan T Leong
(74) *Attorney, Agent, or Firm* — Nguyen & Tarbet Law Firm

(57) ABSTRACT

A device for interfacing coatings, the device comprising at least one well each comprising an elastomeric bottom surface. At least one slit is formed on the elastomeric bottom surface. At least one removable divider is removably inserted into the at least one slit, whereby at least one gap is created and the at least one well is divided into at least two compartments. A designated coating is lined on the elastomeric bottom surface of each of the at least two compartments. Removal of the at least one removable divider then causes the at least one gap to close, allowing for the designated coatings lined on the elastomeric bottom surface of each of the at least two compartments to interface with each other.

14 Claims, 6 Drawing Sheets
(4 of 6 Drawing Sheet(s) Filed in Color)

(51) Int. Cl.
*C12M 1/00* (2006.01)
*C12M 1/26* (2006.01)
*C12M 1/42* (2006.01)
*C12N 1/00* (2006.01)

(56) References Cited

U.S. PATENT DOCUMENTS

| | | | |
|---|---|---|---|
| 2005/0158880 A1* | 7/2005 | Ostuni | B01J 19/0046 438/1 |
| 2006/0270032 A1 | 11/2006 | Bhatia et al. | |
| 2008/0220169 A1 | 9/2008 | Khademhosseini et al. | |
| 2014/0323330 A1* | 10/2014 | Bergo | G01N 33/54306 506/9 |

OTHER PUBLICATIONS

D. Falconnet, G. Csucs, H.M. Grandin, M. Textor (2006) Surface engineering approaches to micro-pattern surfaces for cell-based assays. Biomaterials 27, 3044-3063.
E.E. Hui, S.N. Bhatia (2007) Proc Natl Acad Sci USA 104, 5722-5726.
H. Kaji, T. Yokoi, T. Kawashima, M. Nishizawa (2008) Lab Chip 9, 427-432.
S.N. Bhatia, M.L. Yarmush, M. Toner (1997) J Biomed Mater Res 34, 189-199.
E. Ostuni, R. Kane, C.S. Chen D.E. Ingber, G.M. Whitesides (2000) Langmuir 16, 7811-7819.
A. Folch, B.H. Jo, O. Hurtado, D.J. Beebe, M. Toner (2000) J Biomed Mater Res 52, 346-353.
J. Tien, C.M. Nelson, C.S. Chen (2002) Proc Natl Acad Sci USA 99, 1758-1762.
A. Khademhosseini, K.Y. Suh, J.M. Yang, G. Eng, J. Yeh, S. Levenberg, R. Langer (2004) Biomaterials 25, 3583-3592.
D. Wright, B. Rajalingam, S. Selvarasah, M.R. Dokmeci, A. Khademhosseini (2007) Lab Chip 7, 1272-1279.
M. Yamato, O.H. Kwon, M. Hirose, A. Kikuchi, T. Okano (2001) J Biomed Mater Res 55, 137-140.
X. Cheng, Y. Wang, Y. Hanein, K.F. Bohringer, B.D. Ratner (2004) J Biomed Mater Res A 70A, 159-168.
M.N. Yousaf, B.T. Houseman, M. Mrksich (2001) Proc Natl Acad Sci USA 98, 5992-5996.
D.T. Chiu, N.L. Jeon, S. Huang, R.S. Kane, C.J. Wargo, I.S. Choi, D.E. Ingber, G.M. Whitesides (2000) Proc Natl Acad Sci USA 97, 2408-2413.
C.T. Ho, R.Z. Lin, W.Y. Chang, H.Y. Chang, C.H. Liu (2006) Lab Chip 6, 724-734.
A.P. Wong, R. Perez-Castillejos, J.C. Love, G.M. Whitesides 2008 Biomaterials 29, 1853-1861.
http://www.sigmaaldrich.com/catalog/substance/nunclabtekchamberslidesystem1234598765?lang=en&region=US.
http://ibidi.com/xtproducts/en/ibidi-Labware/Open-Slides-Dishes:-Removable-Chambers/Culture-Insert-2-Well.
http://www.cellbiolabs.com/wound-healing-assays.

* cited by examiner

METHOD AND DEVICE FOR PATTERNING AN INTERFACE

CROSS REFERENCE

This application claims priority to U.S. Provisional Patent Application No. 62/153,420, filed Apr. 27, 2015, the specification(s) of which is/are incorporated herein in their entirety by reference.

BACKGROUND OF THE INVENTION

Cell-cell interactions are essential to regulating the behavior and function of cells and tissues. Cell micro-patterning has become a very useful technique in cell biology, allowing precise control over the spatial organization of cell populations in vitro. This has enabled new types of experiments to be performed and unique insights into tissue biology. However, these techniques are typically developed in engineering laboratories, and high-quality patterning tools are not easily accessible to users with conventional training in cell biology.

The patterning of a sharp interface between two different cell populations, with direct cell-cell contact between the two populations, is useful for a number of different biological studies. A variety of tissue systems exhibit phenotypic differences when two different cell populations are mixed and allowed to interact. These include liver hepatocytes and non-parenchymal liver cells, endothelial and smooth muscle vascular cells, neurons and glial cells, neurons and meningeal cells, stem cells and feeder layers, and tumor and host stromal cells. A sharp patterned interface between two populations allows investigation of the role of direct cell-cell contact, gradients in cell signaling, migration and invasion between populations, morphogenesis, scarring and fibrosis, and other forms of cell-cell crosstalk.

There are two typical methods of patterning cell populations. The first requires sequential seeding, wherein one population of cells is patterned first, and later a second population of cells is added to fill in the unoccupied regions. Patterning of the first population is often accomplished by micro-contact printing of an adhesive protein, the use of a removable stencil, or microfluidic channels. See reference [1]. The challenge with this approach is that some cells from the second population attach in regions occupied by the first population, resulting in cross-contamination.

The second approach requires cell migration following removal of a barrier. The two cell populations are seeded simultaneously in two separate regions, with a removable barrier in between. After cell attachment, the barrier is removed and the cells can migrate towards each other to form a contact interface. The challenge with this approach is that the width of the barrier is often hundreds of micrometers. Thus, the cells have to travel quite a distance before the two populations interface. By the time this gap is closed (which may take up to 48 hours), the interface may be ragged and not very sharp.

To address the aforementioned challenges, another class of devices consists of discrete plates that are first seeded with different cell types and then moved together to form a sharp cell-cell interface. This approach also allows cells to grow to confluence and reach a quiescent state prior to the initiation of co-culture. In addition, the cell patterning is more precise using this latter approach. Each region is exposed to only one cell type, minimizing cross-contamination, and the interface is formed without relying on cell migration, ensuring sharp boundaries. See reference [2] and reference [3].

The method described in [2] utilizes a silicon substrate, which is not optically transparent. This makes the system incompatible with the inverted microscopes that are most widely employed in biology laboratories. On the other hand, although the method described in [3] employs transparent substrates, there is no firm locking mechanism to ensure accuracy in horizontal and vertical alignment.

Importantly, neither reference [2] nor reference [3] are easy to use or follow for those with standard training in cell biology. Furthermore, while some of the techniques are simpler, the quality of the patterned cell interface is not as good. Thus, there is a strong need for a low-cost and easy-to-use method to pattern a sharp interface between cell populations.

Any feature or combination of features described herein are included within the scope of the present invention provided that the features included in any such combination are not mutually inconsistent as will be apparent from the context, this specification, and the knowledge of one of ordinary skill in the art. Additional advantages and aspects of the present invention are apparent in the following detailed description and claims.

SUMMARY OF THE INVENTION

A number of commercial vendors sell stencil-like devices that can be used for cell patterning. These devices include the Ibidi microwell culture inserts, the Nunc Lab-Tek Chamber Slides, and the CytoSelect Wound Healing Assay from Cell Biolabs. All of these devices use a removable insert that is sealed onto a glass slide or a standard cell culture dish, and pattern cell co-cultures by sequential seeding of different cell populations or simultaneous seeding followed by cell migration.

Referring to FIG. 1, cell patterning comparison between the present invention and the Ibidi microwell culture inserts is shown. Both sequential seeding and simultaneous seeding were used with the Ibidi device. Referring to FIG. 1-B, when sequential seeding was performed on the Ibidi device, there was heavy contamination of the second-seeded population into the first. Referring to FIG. 1-C, when simultaneous seeding was performed on the Ibidi device, the cells were much more spaced out and no longer confluent by the time the two populations migrated together. Consequently, there is significantly less cell-cell contact between the two populations at the interface.

The present invention features a method and device that addresses the need for a low-cost and easy-to-use method and device to pattern a sharp interface between two or more cell populations or, more generally, two or more coatings wherein their interfacing properties are of interest.

The invention takes advantage of the elastic properties of elastomeric materials such as, for example, polydimethylsiloxane (PDMS). A small slit is cut into an elastomeric bottom surface of a well (e.g., cut down the middle of the elastomeric bottom surface). The well is stretched to open the slit to form a gap, and a barrier is then inserted into the slit to split the well into two separate compartments. Two coatings of cell suspensions or other particles or species (e.g., protein suspensions or chemical reagents) are disposed into each compartment. After removing any unbound species or cells from each of the compartments, the barrier is removed to allow the gap in the elastomeric bottom surface to close, thereby leaving a sharp interface between the two cell populations (or other particles or species). The separated regions are rejoined with near perfect accuracy, creating a continuous surface with a sharp transition between two different surface treatments. Referring to FIG. 2, the process described above is shown.

Referring to FIG. 1-A, the present invention surprisingly achieved a sharp interface with little cross-contamination. The method is simple to follow and is capable of creating an interface between the compartment populations that is very sharp and clean, with the two cell populations (or other surface deposited species) in direct contact and having no cross-contamination. To a conventional biologist, the system resembles a standard tissue culture plate. Preparation simply involves pipetting into open wells. Imaging is standard as the device is transparent and can thus be used on a standard biological microscope. The method improves accuracy of the interface created, eases the interface creating procedure, increases robustness of the interface creating process, decreases the price of interface creation, and/or allows easier imaging of the interface on a standard microscope.

BRIEF DESCRIPTION OF THE DRAWINGS

This patent application contains at least one drawing executed in color. Copies of this patent or patent application publication with color drawing(s) will be provided by the Office upon request and payment of the necessary fee.

DESCRIPTION OF PREFERRED EMBODIMENTS

Figure 1:
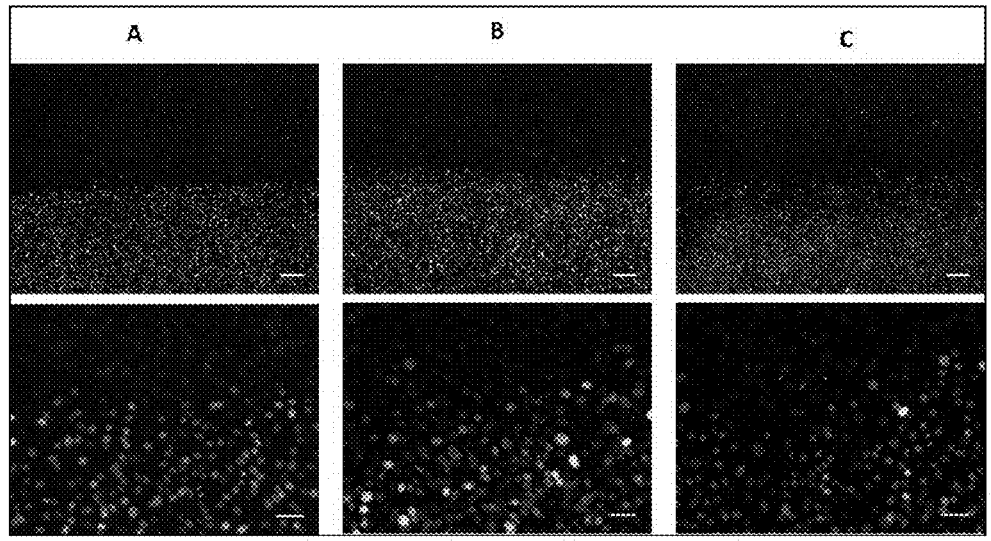
FIG. 1 shows a cell patterning comparison between the present invention and the Ibidi microwell culture inserts.

Following is a list of elements corresponding to a particular element referred to herein:
999 coating interfacing device
100 well
110 well first compartment
120 well second compartment
130 well compartments
200 elastomeric bottom surface
210 first elastomeric bottom surface
220 second elastomeric bottom surface
300 slit
310 gap
400 divider
500 spacer
510 aperture The term "coating" as used herein broadly refers to items including but not limited to macrostructures, microstructures, molecules, cells, proteins, chemicals, paints, acids, bases, etchants, cross-linkers, or any component that is observed along with and used in accordance with this present invention. For example, a designated coating on a surface may be a layering of a specific type of cells on that surface. Different surfaces, e.g. different elastomeric bottom surfaces, may have different or same designated coatings. For example, a first elastomeric bottom surface may be layered with one type of cells, and a second elastomeric bottom surface may be layered with a type of cells that are different from the ones on the first elastomeric bottom surface.

Figure 3:
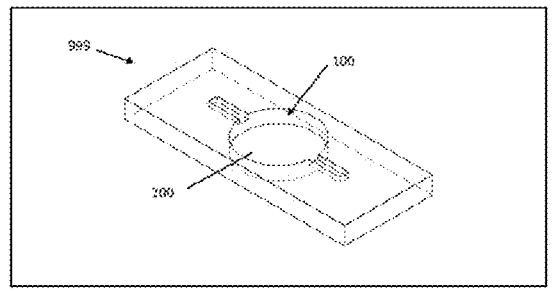
FIG. 3 shows the well (100) comprising an elastomeric bottom surface (200).

Referring to FIG. 3, in some embodiments, a coating interfacing device (999) comprises a well (100) with an elastomeric bottom surface (200) (For example, Polydimethylsiloxane, PDMS). In some embodiments, the entire well (100) is composed of elastomeric material. In some embodiments, elastomeric materials used in accordance with the present invention could be any material with elastomeric or partially elastomeric properties, including but not limited to silicone rubbers, fluoroelastomers, polyacrylic rubbers, isoprene rubbers, butyl rubbers, polyurethanes, and liquid crystal elastomers.

Figure 4:
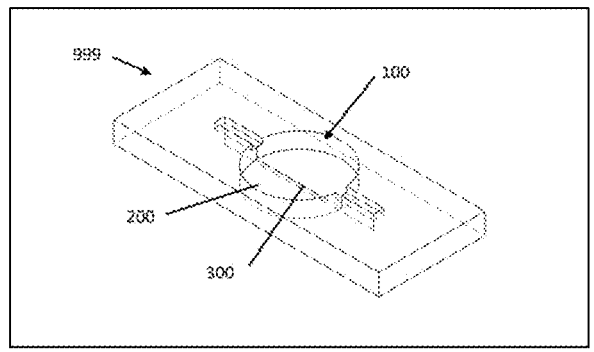
FIG. 4 shows the elastomeric bottom surface (200) with a slit (300).

Referring to FIG. 4, a slit (300) cut into the elastomeric bottom surface (200) is shown. In some embodiments, the slit (300) may be cut down the middle of the well (100) to form two equally-sized regions within the well (100). In other embodiments, the slit (300) does not make equally-sized regions.

Figure 2:
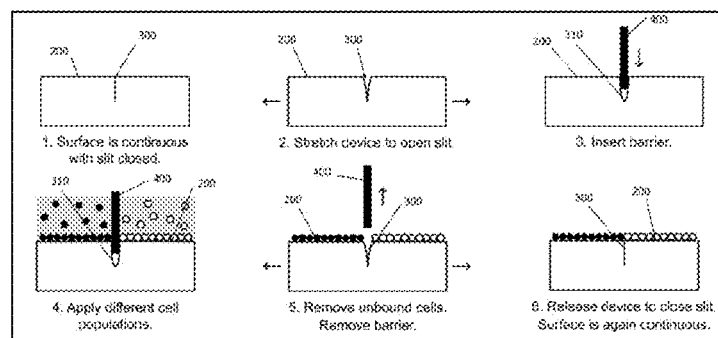
FIG. 2 shows the process of the present invention.
Figure 5A:
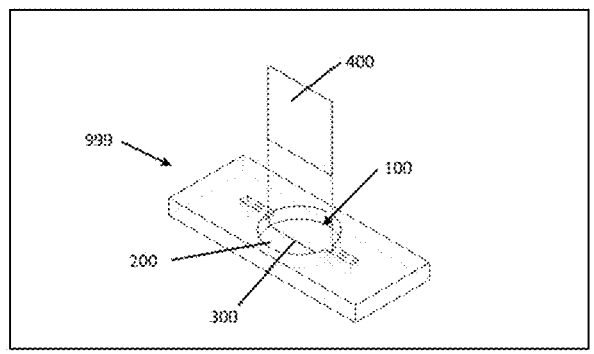
FIG. 5A shows the divider (400) positioned over the slit (300).
Figure 5B:
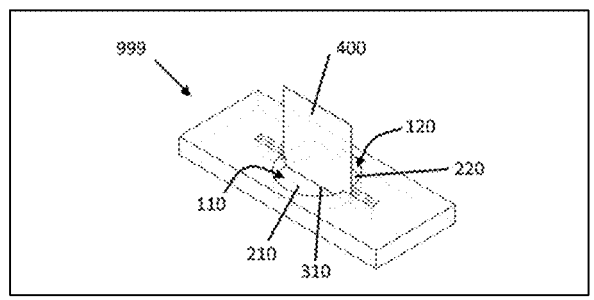
FIG. 5B shows the divider (400) inserted into the slit (300).

Referring to FIG. 5A and FIG. 5B, a removable divider (400) (for example, a glass coverslip) inserted into the slit (300) to create a gap (310) and two separate compartments, a well first compartment (110) and a well second compartment (120), is shown. After each compartment is layered with a coating and any unbound coating within each compartment is removed, the glass coverslip (400) is removed to allow the elastic properties of the PDMS to close the gap (310). As the gap (310) closes, the coating within each compartment is brought together to form a sharp interface. Referring to FIG. 2, the process described above is shown.

Device Construction

Figure 6:
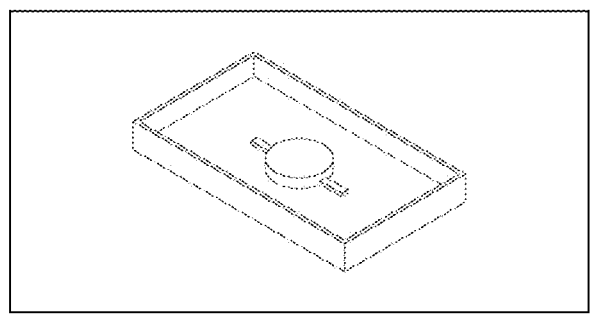
FIG. 6 shows a mold that is used to cast the well (100).

In some embodiments, the coating interfacing device (999) construction is as follows: a mold made from laser-cut acrylic pieces adhered to the bottom of a polystyrene petri dish (FIG. 6) is created. PDMS pre-polymer is mixed and degassed, then poured into the mold of FIG. 1 and cured in an oven at 65° C. overnight. The cured well (100) (FIG. 3) is then carefully removed and cut from the mold. Finally, the slit (300) is cut into the middle of the elastomeric bottom surface (200) using a rigging device such as one shown in FIG. 7. In this case, the rigging device holds a disposable straight razor blade at a fixed height relative to the rigging device base, such that slits (300) of reproducible length and depth are produced on the elastomeric bottom surface (200). Optional wings may be extended out from the top edge of the well (100) (as shown in FIG. 3, FIG. 4, FIG. 5A, and FIG. 5B) in order to make the slit (300) easier to open for divider (400) insertion.

The Rigging Device

Figure 7:
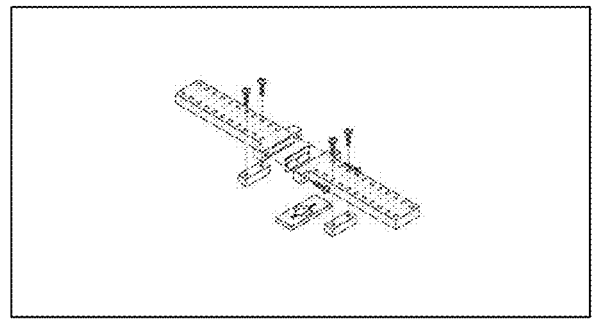
FIG. 7 shows a rigging device used to form the slit (300) on the elastomeric bottom surface (200).

In some embodiments, the rigging device such as one shown in FIG. 7 used to cut the slit (300) in the elastomeric bottom surface (200) includes a razor blade that is held between two mounting pieces that squeeze to secure the razor blade. The rigging device includes two feet that are dimensioned to adjust the depth of the cut of the slit (300) into the elastomeric bottom surface (200). Typically, the thickness of the well (100) at the elastomeric bottom surface (200) is around 1-2 mm (the total or maximum thickness of the well (100) at the thickest part may be on the order of 1 cm). The slit (300) should not cut entirely through the elastomeric bottom surface (200) but rather a portion thereof. For example, the slit (300) may be cut in less than ⅔ of the thickness of the elastomeric bottom surface (200) of the well (100) although various depths may be used. Again, the depth of penetration can be adjusted by varying the thickness of the feet.

Multi-Well Configuration

Figure 8:
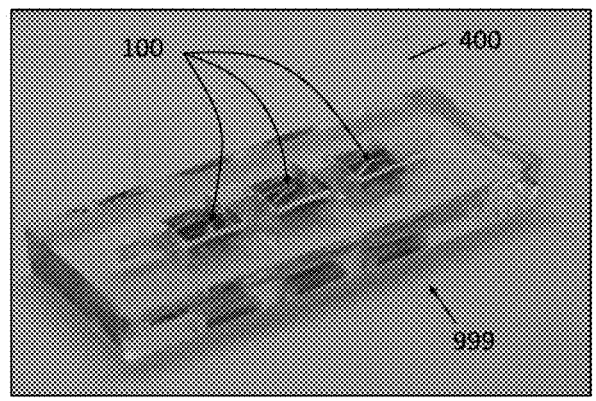
FIG. 8 shows a multi-well device (999). In this embodiment, there are 3 wells (100) and a single divider (400) is used for all 3 wells (100).

Multi-well culture formats are often preferred in cell biology in order to perform replicates of multiple conditions in parallel. Thus, in some embodiment, multiple wells (100) are molded on the same surface and a single slit (300) extending over each of the elastomeric bottom surfaces (200) of the multiple wells (100) is cut, allowing a single divider (400) to divide each of the multiple wells (100) into a well first compartment (110) and a well second compartment (120) at a time. An example of this embodiment is shown in FIG. 8.

Multiple Slits

Figure 9A:
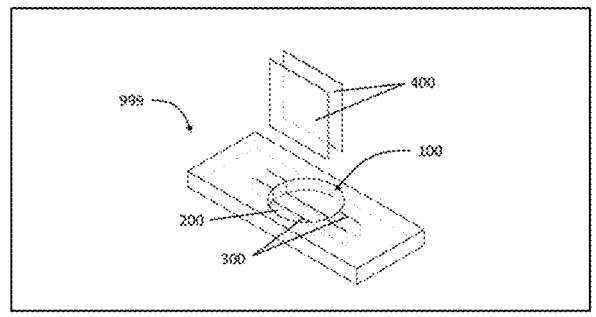
FIG. 9A and FIG. 9B show an elastomeric bottom surface (200) cut with two parallel slits (300). Dividers (400) inserted into these slits (300) create three compartments (130).
Figure 9B:
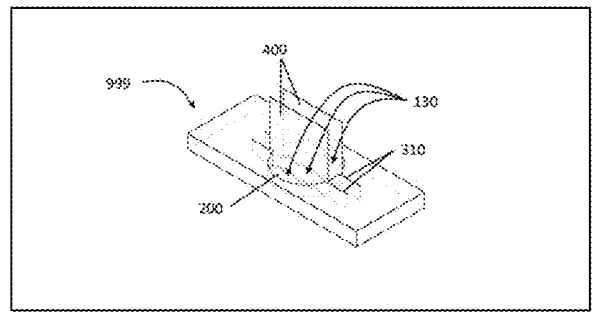

Referring to FIG. 9A and FIG. 9B, in some embodiment, multiple slits (300) can be cut in a single elastomeric bottom surface (200). The slits (300) could be cut simultaneously with multiple blades mounted on the rigging device. A separate divider (400) would be inserted into each slit (300). For example, two parallel slits (300) each with a divider (400) inserted therein would divide the well (100) into three separate compartments (130), each of which would have a designated coating. This would then allow two adjoining interfaces between the three designated coatings once the dividers (400) are removed. The well (100) could be divided into any number of compartments (130) in this alternative embodiment.

Visual Features

Figure 10:
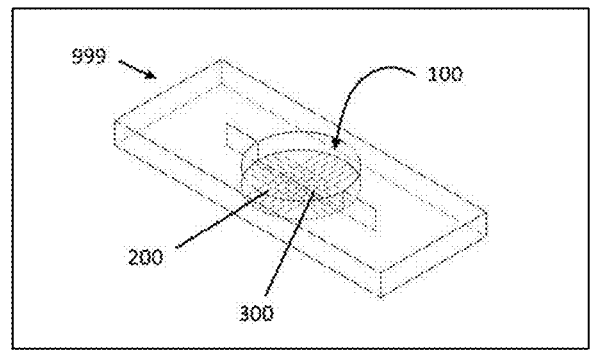
FIG. 10 shows orientation marks molded into the elastomeric bottom surface (200), assisting the process of indexing cells by location.

Referring to FIG. 10, in some embodiments, one or more visual features can be formed on the elastomeric bottom surface (200). This may be desirable when the same cell populations are put under repeated rounds of microscope imaging and individual cells need to be identified. Raised or indented surfaces can be added on the mold, such that when the well (100) is made from the mold, the features are transferred to the well (100). Raised surfaces on the mold would be cast as engravings on the elastomeric bottom surface (200), and indented surface on the mold would be cast as embossments on the elastomeric bottom surface (200). The casted features can include but is not limited to an array of dots, an array of letters or numbers, or a grid pattern.

Maintaining Distance Between Coatings

Figure 11:
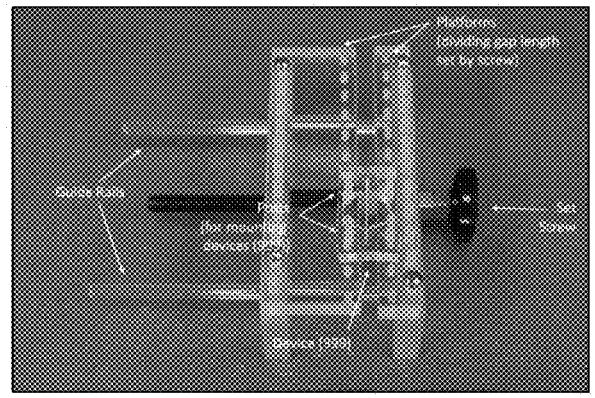
FIG. 11 shows an adjustable clamp mechanism that can maintain the distance between the coatings disposed within the well device (999).
Figure 12A:
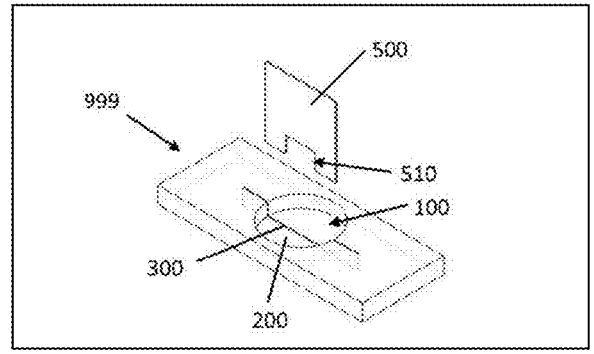
FIG. 12A shows a spacer (500) comprising an aperture (510) inserted into the slit (300) after removing the divider (400) to fluidly connect the first compartment (110) and the second compartment (120).
Figure 12B:
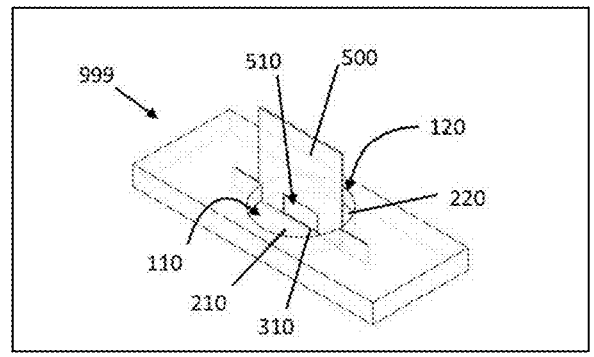
FIG. 12B shows the spacer (500) inserted into the slit (300).
Figure 15A:
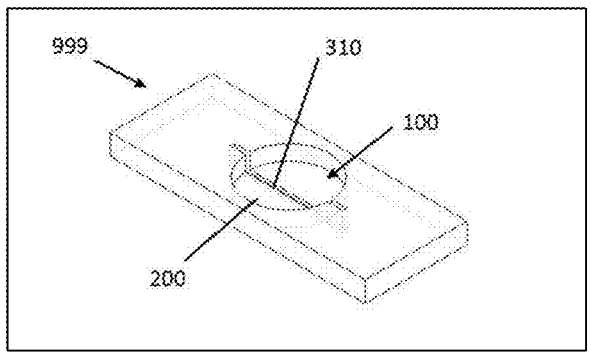
FIG. 15A and FIG. 15B show a well (100) with a wide gap that allows for exchange of diffusible factors between the designated coatings in the first compartment (110) and the designated coatings in the second compartment (120).
Figure 15B:
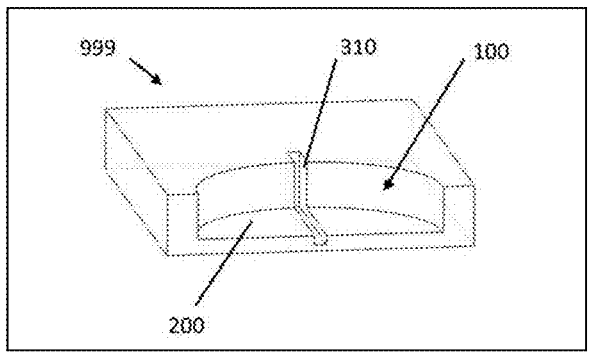

In some embodiments, it may be desirable to maintain a gap (310) between the coatings after removing the divider (400). In a non-limiting example, this would enable studies of soluble factor exchange independent of cell-cell contact. One embodiment of achieving this is to create a permanent gap (310) as shown in FIG. 15A and FIG. 15B. In another embodiment derived from the present invention, an adjustable clamp shown in FIG. 11 holds the well first compartment (110) and the well second compartment (120) at a set and controllable distance. Two moveable acrylic platforms with thin cylindrical posts are mounted on parallel rails, and turning a central set screw adjusts the distance between the two platforms. The PDMS well device (999) can be mounted on posts formed on the respective platforms such that increasing and decreasing the distance between the two platforms opens and closes the slit (300) interface. Long-term automated actuation may be achieved by addressing the set screw using a stepper motor and microcontroller, potentially enabling studies of coating-to-coating interactions across dynamically varying interface distances. Alternatively, the gap (310) could be held open by placing a spacer (500) in the gap to keep it from reclosing. Unlike the divider (400) in FIG. 5A and FIG. 5B, in some embodiments, the spacer (500) is applied only on the two ends of the slit (300) to fluidly connect the well first compartment (110) and the well second compartment (120). This allows paracrine communication across the gap (310). An embodiment of the spacer (500) is shown in FIG. 12A and FIG. 12B.

Non-Limiting Example

In a non-limiting example using cells as the coating of interest, a method for preparing a device (999) with a single slit (300) for interfacing experiments is presented below; devices (999) with multiple slits (300) are prepared with a similar procedure: the device (999) is placed into a polystyrene petri dish and sterilized via ultraviolet (UV) light exposure overnight. The removable divider (for example, glass coverslips) (400) is also sterilized either via autoclaving or UV exposure. After sterilization, the device well (100) is treated with fibronectin (or other extra cellular matrix components) at room temperature for approximately 3 hours. Excess fibronectin is then removed and the device (999) is rinsed 1 time with sterile phosphate buffered saline (PBS).

Once the device (999) is rinsed, the device (999) is flexed or bent apart such that the pre-cut slit (300) on the elastomeric bottom surface (200) is exposed to form a gap (310). The sterile glass coverslip (400) is then inserted into the gap (310) (FIGS. 5A and 5B). A glass coverslip (400) is inserted after the fibronectin treatment to prevent the fibronectin from adsorbing to the glass coverslip (400) surface, which could lead to cell adhesion to the glass coverslip (400). Cells are then seeded (coated) into each of the well first compartment (110) and the well second compartment (120) for at least 3 hours, effectively coating the well first compartment (110) and the well second compartment (120). Once the cells are adhered to the surfaces within the well (200) and any unbound coating is removed from the first compartment (110) and the second compartment (120), the sides of the device (999) are flexed or bent apart again to remove and discard the glass coverslip (400). As the gap (310) closes, the coatings within each compartment touch and thus interface.

Figure 13:
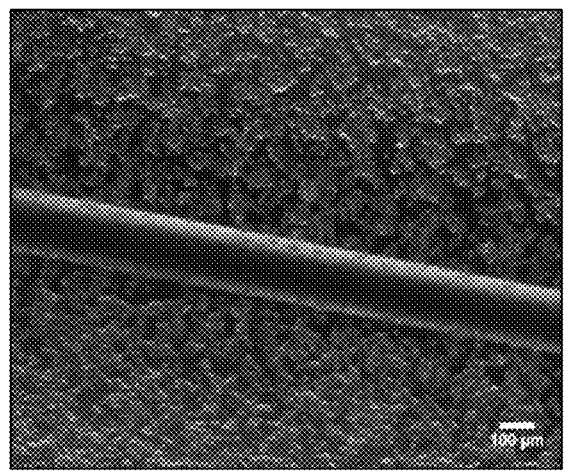
FIG. 13 shows a microscope image of patterned cells with the divider (400) in place.
Figure 14A:
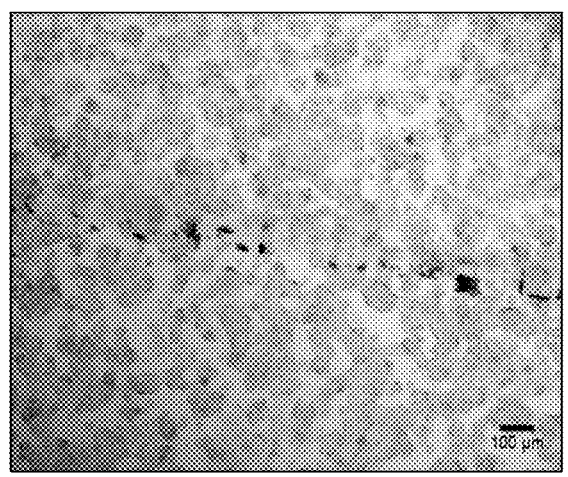
FIG. 14A shows a brightfield image of patterned cells with the divider (400) removed.
Figure 14B:
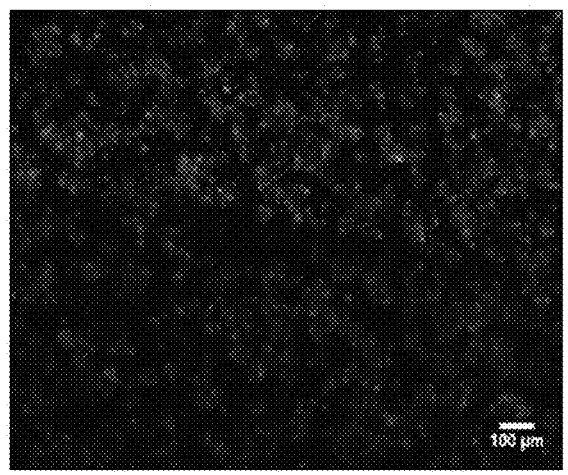
FIG. 14B shows an epi-fluorescence image of patterned cells with the divider (400) removed.

FIG. 13 shows a microscope image of cell populations separated by the glass coverslip (400) in place. FIG. 14A and FIG. 14B show the patterned cell populations with the glass coverslip barrier (400) removed. FIG. 14A shows a brightfield image and FIG. 14B shows an epi-fluorescence image.

As used herein, the term "about" refers to plus or minus 10% of the referenced number.

Various modifications of the invention, in addition to those described herein, will be apparent to those skilled in the art from the foregoing description. Such modifications are also intended to fall within the scope of the appended claims. Each reference cited in the present application is incorporated herein by reference in its entirety.

Although there has been shown and described the preferred embodiment of the present invention, it will be readily apparent to those skilled in the art that modifications may be made thereto which do not exceed the scope of the appended claims. Therefore, the scope of the invention is only to be limited by the following claims. Reference numbers recited in the claims are exemplary and for ease of review by the patent office only, and are not limiting in any way. In some embodiments, the figures presented in this patent application are drawn to scale, including the angles, ratios of dimensions, etc. In some embodiments, the figures are representative only and the claims are not limited by the dimensions of the figures. In some embodiments, descriptions of the inventions described herein using the phrase "comprising" includes embodiments that could be described as "consisting of", and as such the written description requirement for claiming one or more embodiments of the present invention using the phrase "consisting of" is met.

The reference numbers recited in the below claims are solely for ease of examination of this patent application, and are exemplary, and are not intended in any way to limit the scope of the claims to the particular features having the corresponding reference numbers in the drawings.

REFERENCES

[1] D Falconnet, G Csucs, H M Grandin, M Textor (2006) Surface engineering approaches to micro-pattern surfaces for cell-based assays. Biomaterials 27, 3044-3063.
[2] E E Hui, S N Bhatia (2007) Proc Natl Acad Sci USA 104, 5722-5726
[3] H Kaji, T Yokoi, T Kawashima, M Nishizawa (2008) Lab Chip 9, 427-432.

What is claimed is:

1. A coating interfacing device (999) for forming a defined interface between separated coatings, the device (999) comprising:
    a well (100) comprising an elastomeric bottom surface (200),
    a slit (300) formed into the elastomeric bottom surface (200),
    a removable divider (400) inserted into the slit (300) to create a closeable gap (310) and to divide the well (100) into a first compartment (110) and a second compartment (120), wherein the first compartment (110) comprises a first elastomeric bottom surface (210) and the second compartment (120) comprises a second elastomeric bottom surface (220),
    the first elastomeric bottom surface (210) and the second elastomeric bottom surface (220) each lined with a designated coating,
    wherein the divider (400) is removed to close the gap (310), whereby the designated coating lined on the first elastomeric bottom surface (210) interfaces with the designated coating lined on the second elastomeric bottom surface (220).

2. The device of claim 1, wherein the elastomeric bottom surface (200) comprises PDMS.

3. The device of claim 1, wherein the coating interfacing device (999) comprises a plurality of wells (100) each comprising an elastomeric bottom surface (200).

4. The device of claim 3, wherein the divider (400) is dimensioned to span and to be inserted into the slit (300) of at least one of the elastomeric bottom surfaces (200).

5. The device of claim 1, wherein the first elastomeric bottom surface (210) and the second elastomeric bottom surface (220) are lined with different designated coatings.

6. The device of claim 1, wherein the first elastomeric bottom surface (210) and the second elastomeric bottom surface (220) are lined with the same designated coating.

7. The device of claim 1, wherein a spacer (500) comprising an aperture (510) is inserted into the slit (300) after removing the divider (400), whereby the first compartment (110) and the second compartment (120) are fluidly connected.

8. A coating interfacing device (999) for forming a defined interface between separated coatings, the device (999) comprising:
    a well (100) comprising an elastomeric bottom surface (200),
    at least one slit (300) formed into the elastomeric bottom surface (200),
    at least one removable divider (400) inserted into the at least one slit (300) to create at least one closeable gap (310) and to divide the well (100) into at least two compartments (130), wherein each compartment (130) comprises an elastomeric bottom surface (200),
    the elastomeric bottom surface (200) lined with a designated coating,
    wherein the at least one divider (400) is removed to close the at least one gap (310), whereby the designated coatings lined on the elastomeric bottom surface (200) of each of the at least two compartments (130) interface with each other.

9. The device of claim 8, wherein the elastomeric bottom surface (200) comprises PDMS.

10. The device of claim 8, wherein the coating interfacing device (999) comprises a plurality of wells (100) each comprising an elastomeric bottom surface (200).

11. The device of claim 10, wherein the at least one divider (400) is dimensioned to span and to be inserted into the at least one slit (300) of at least one of the elastomeric bottom surfaces (200).

12. The device of claim 8, wherein the elastomeric bottom surface (200) of each of the at least two compartments (130) are lined with different designated coatings.

13. The device of claim 8, wherein the elastomeric bottom surface (200) of each of the at least two compartments (130) are lined with the same designated coating.

14. The device of claim 8, wherein at least one spacer (500) each comprising an aperture (510) is inserted into the at least one slit (300) after removing the at least one divider (400), whereby each of the at least two compartments (130) are fluidly connected to each other.

* * * * *